United States Patent [19]

Birch et al.

[11] Patent Number: 4,686,371
[45] Date of Patent: Aug. 11, 1987

[54] APPARATUS FOR MEASURING FLUORESCENCE DECAY CHARACTERISTICS OF MATERIALS

[75] Inventors: David J. S. Birch; Robert E. Imhof, both of Glasgow, Scotland

[73] Assignee: University of Strathclyde, Glasgow, Scotland

[21] Appl. No.: 778,451

[22] PCT Filed: Jan. 21, 1985

[86] PCT No.: PCT/GB85/00028

§ 371 Date: Sep. 18, 1985

§ 102(e) Date: Sep. 18, 1985

[87] PCT Pub. No.: WO85/03352

PCT Pub. Date: Aug. 1, 1985

[30] Foreign Application Priority Data

Jan. 21, 1984 [GB] United Kingdom ............... 8401672

[51] Int. Cl.$^4$ ........................................... G01N 21/64
[52] U.S. Cl. ............................... 250/461.1; 356/318
[58] Field of Search ............. 250/458.1, 461.1, 461.2; 356/317, 318

[56] References Cited

PUBLICATIONS

Birch et al., "Differential Pulse Fluorometry Using Photomultipliers", *Journal of Physics E: Sci. Intr.*, vol. 17, No. 5, May 1984, pp. 417–418.
Birch et al., "A Single Photon Counting Fluorescence Decay Time Spectrometer", *Jour. of Physics E: Sci. Inst.*, vol. 10, No. 10, Oct. 1977, pp. 1044–1049.
Rayner et al., "Correction of Instrumental Time Response Variation with Wavelength in Fluorescence Lifetime Determination", *Rev. of Sci. Inst.*, vol. 48, No. 8, Aug. 1977, pp. 1050–1054.
Wijnandts van Resandt et al., "Double Beam Fluorescence Lifetime Spectrometer with Subnanosecond Resolution", *Rev. of Sci. Instr.*, vol. 53, No. 9, Sep. 1982, pp. 1392–1397.

Primary Examiner—Janice A. Howell
Attorney, Agent, or Firm—Pennie & Edmonds

[57] ABSTRACT

The invention provides an apparatus for measuring fluorescence characteristics of a sample material located at a sample station (3) comprising a fluorescence photon-event receiving means (9), an excitation light source (1) and a means (13, 14, 16) for determining the pulse profile of the excitation light. Detecting means (10) is coupled to receive the output of receiving means (9) and the output of the determining means (13, 14, 16) and synchronization means (4, 6, 7) is operable by the excitation light source to generate synchronization pulses for controlling operation of a measuring means (8, 12) which is coupled to the detecting means (10) and which is operable according to the photon correlation technique to provide on a time-shared basis a measure of the fluorescence characteristics and a measurement of the pulse profile.

9 Claims, 5 Drawing Figures

APPARATUS FOR MEASURING FLUORESCENCE DECAY CHARACTERISTICS OF MATERIALS

This invention relates to apparatus for measuring fluorescence decay characteristics (referred to hereinafter simply as 'fluorescence characteristics') of materials.

Apparatus for measuring fluorescence characteristics of a material is already known and comprises a light source (either narrow band or monochromatic), and hereinafter referred to as an excitation light source, capable of emitting a train of light pulses which are directed onto the material (or sample) under test to excite that sample into a fluorescent state. When the sample fluorescences it emits energy in the form of single photons and the known apparatus comprises photon detection and measuring systems, the latter functioning according to the well-known photoncorrelation technique using synchronisation pulses derived from the excitation light source, whereby fluorescence decays and decay times for the sample (and associated properties such as anisotropy decay) are evaluated.

In practise typical excitation light sources are flashlamps (with associated waveband filters) and lasers both of which suffer from long-term time-dependent changes in their optical pulse profile and it is therefore necessary to measure the excitation pulse profile applied to each sample. In the known apparatus this is undertaken either immediately before or immediately after irradiation of the sample by substituting at the sample station a reflective device or scatterer so that the reflected excitation is directed into the detection and measuring systems. In consequence certain long-term time-dependent changes in the characteristics of the detection and measuring systems are accounted for in addition to long-term excitation pulse profile changes.

The known apparatus suffers from a number of disavantages and it is an object of the present invention to obviate or mitigate these disadvantages. For example, the known apparatus measures the excitation pulse profile before or after sample irradiation and therefore relies upon constancy of excitation pulse profile both during sample irradiation and in continuity with measurement of the excitation pulse profile. In fact known excitation light sources have pulse profiles which tend to vary from pulse to pulse in addition to long-term pulse profile variation. Furthermore, substitution of the sample and reflective device at the sample station requires interchangeability which in fact is not universally practical because certain samples fluoresce under environmental conditions which render the reflective device difficult to substitute. Additionally, fluorescence usually occurs at a spectral wavelength different from (being larger than) that of the excitation and the detection and measuring systems usually have differing characteristics at these two wavelengths so that the assessment of changes in the detection and measuring systems by directing the excitation light through these systems is inherently inaccurate.

According to the present invention there is provided apparatus for measuring fluorescence characteristics of a material sample, said apparatus comprising a sample station for receiving a material sample the fluorescence characteristics of which are to be measured, a fluorescence photon-event receiving means coupled to said sample station to receive single photon events arising therefrom, an excitation light source capable of emitting a train of excitation light pulses towards said sample station so as to irradiate a sample therein, excitation pulse profile determining means sensitive to said train of excitation light pulses and having sufficient attenuation to provide an output event count rate compatible with the fluorescence photon event count rate, detecting means coupled to receive the output of said receiving means and the output of said determining means, synchronisation means operable by said excitation light source to generate a train of synchronisation pulses, measuring means coupled to the output of said detecting means and to the output of said synchronisation means and operable according to the photon correlation technique to provide on a time-shared basis a measure of said fluorescence characteristics and a measure of said excitation pulse profile, said measuring means including discrimination means enabling said excitation pulse profile measure to be distinguished from said fluorescence characteristics measure.

By virtue of the present invention measurement of the excitation pulse profile is effected on a time-shared basis throughout the duration of irradiation of the sample as a result of which the measure is more precise than hitherto and is undertaken without interruption and alteration of the sample station and associated detector so that stringent sample environments can be maintained without disturbance.

The detecting means may comprise a single detector receiving both sets of input events or it may comprise a pair of detectors each receiving only one set of input events. The latter arrangement is preferred because it enables matching of detector transfer functions notwithstanding the different spectral wavelengths of the two sets of input events. Accordingly correction of timing differences is effected automatically.

A time-delay means is preferably provided in one of said receiving means and said determining means, which may be effected optically or electronically, and preferably is arranged to introduce a time-delay of less than one half the pulse repetition period of the excitation light source but substantially greater than the fluorescence decay time of the sample.

The measuring means is arranged to measure the time interval at which an event occurs in relation to a synchronisation pulse and may convert these measures to proportional amplitude measures. Additionally the measuring means measures the accumulated number of events occurring at each time interval over the duration of the measurement process.

The discrimination means may be provided by electronic routing circuitry whereby fluorescence events are directed into different storage channels from excitation pulse profile events or all events may be stored in a single storage channel and discriminated by virtue of excitation pulse profile events occurring and being stored at longer time interval indicia than fluorescence events.

Embodiments of the present invention will now be described by way of example with reference to the accompanying schematic drawings, in which.

Figure 1:
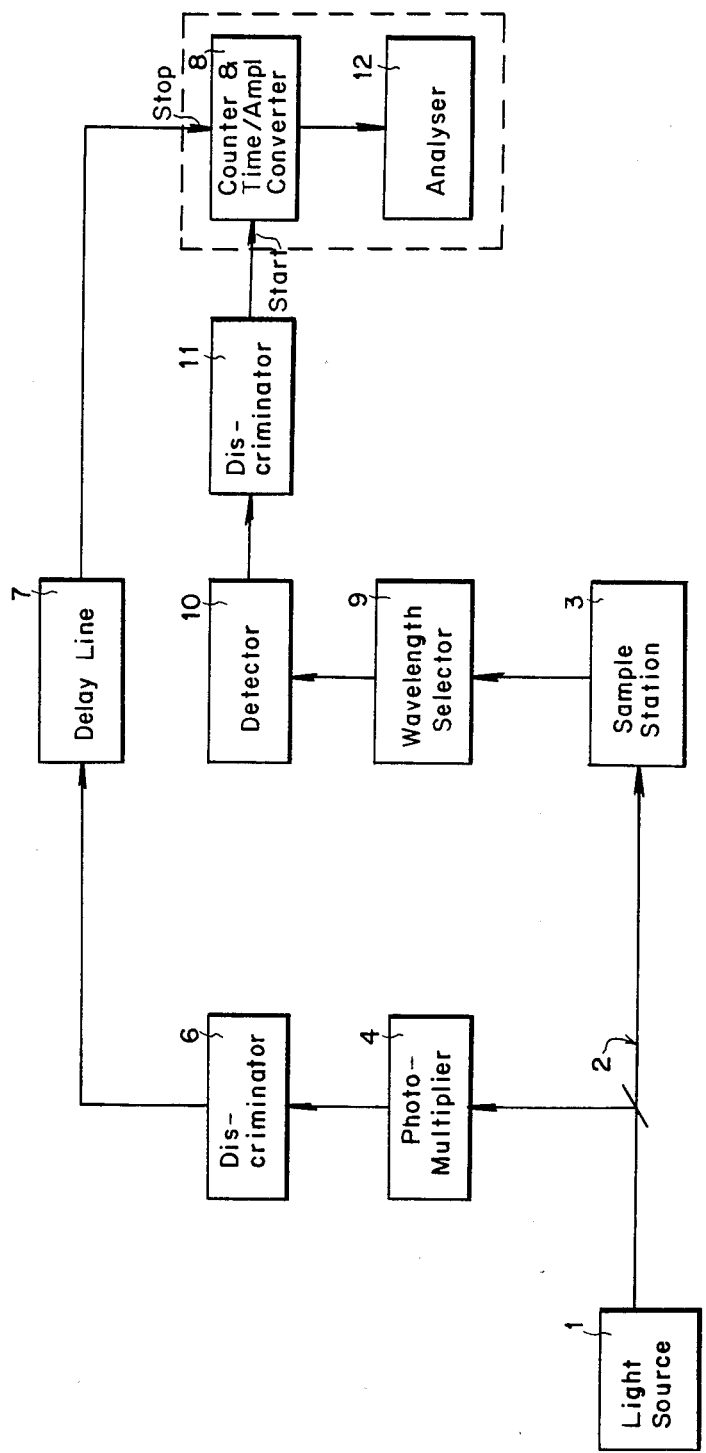
FIG. 1 illustrates the known apparatus for measuring fluorescence characteristics of a sample.

With reference now to FIG. 1 an excitation light source 1 is arranged to emit a train of excitation light pulses along path 2 in order to irradiate a sample in a sample station 3. Fluorescence photon events are received by means 9 which usually is in the form of a wavelength selector such as a grating monochromator the output from which is delivered to a single photon detector 10 (such as a photomultiplier). Detector 10 issues corresponding output signals to one input of a measuring means 8,12 via a threshold discriminator 11 to eliminate spurious signals. Measuring means 8,12 has a second input which is connected to receive a train of synchronisation pulses derived from source 1, and comprises a device 8 which operates as a start/stop counter and time interval to amplitude converter according to the photon correlation technique and a multichannel analyser 12 in which the output from device 8 is stored as a histogram representing the relative probabilities of occurrance of the various start/stop delay times which is a measure of the fluorescence characteristics of the sample. The synchronisation pulses in FIG. 1 are derived from the optical output of source 1 by way of a photomultiplier 4, discriminator 6 and delay line 7 whereby the synchronisation pulses are arranged to occur after respective detected photon events and accordingly photon events are applied to the 'start' input of device 8 whilst synchronisation pulses are applied to the 'stop' input of device 8.

As is known the synchronisation pulses may be derived electrically from the pulse-forming control system of the source 1 and may be operable upon the 'start' input of the device 8. Additionally, of course, the photon correlation technique yields valid results only when a low detection probability is maintained, typically one photon event for each 100 excitation pulses.

Turning now to the embodiments of the present invention as illustrated in FIGS. 2-5 it is to be noted that the components of FIG. 1 are contained therein and retain their respective numerical designations. Thus in FIG. 2 excitation pulse profile determining means is provided in addition to the FIG. 1 components and comprises a beamsplitter 13 located in path 2 whereby a small fraction of the excitation light is delivered to an optical time-delay means 14 (for example an optical path in air (folded between mirrors) or possibly a light guide such as a single mode glass fibre) the output of which is directed by matching optics 16 to the input of detector 10. Accordingly in this embodiment a single detector 10 receives events on a time-shared basis from element 16 and also from element 9. Discrimination between the two measures provided by means 8,12 is achieved in this embodiment by the position within the memory of analyser 12, excitation vents being delayed with respect to fluorescence events.

Figure 2:
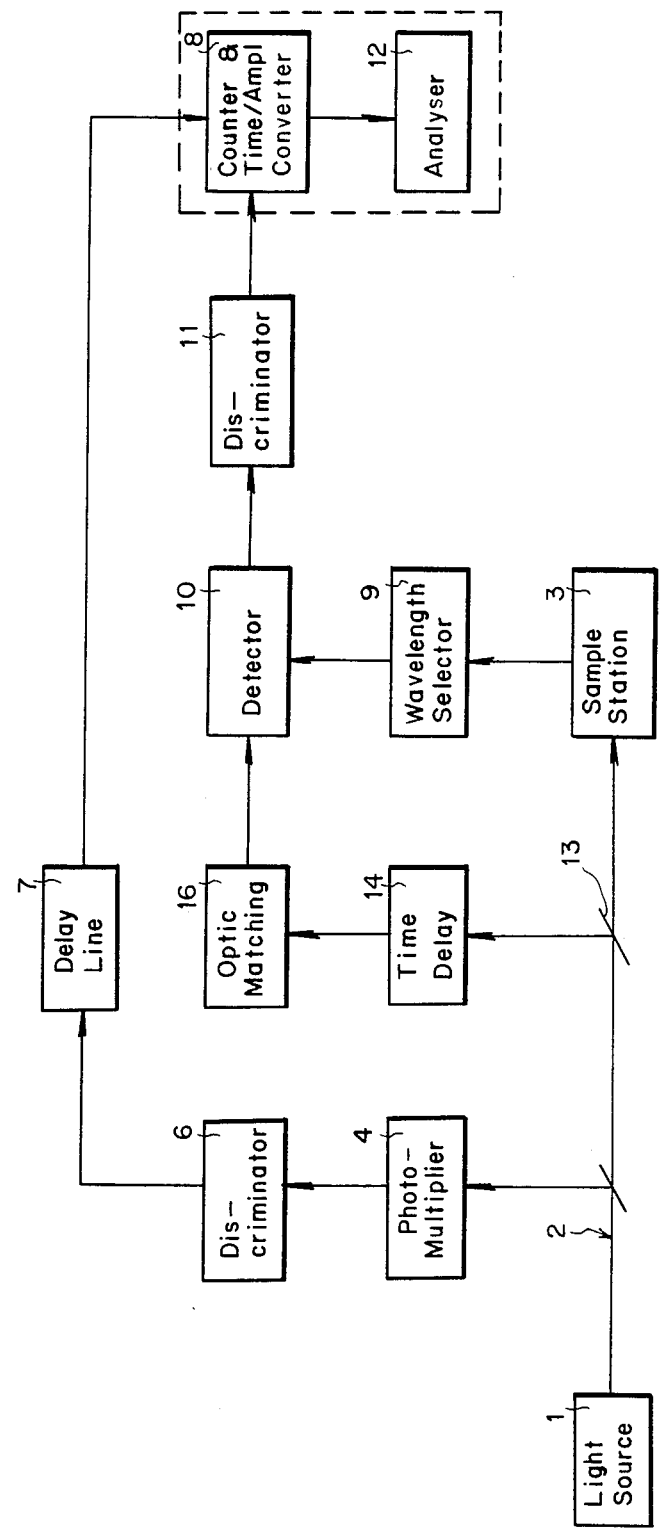
FIG. 2 illustrates a first embodiment of apparatus according to the present invention.
Figure 3:
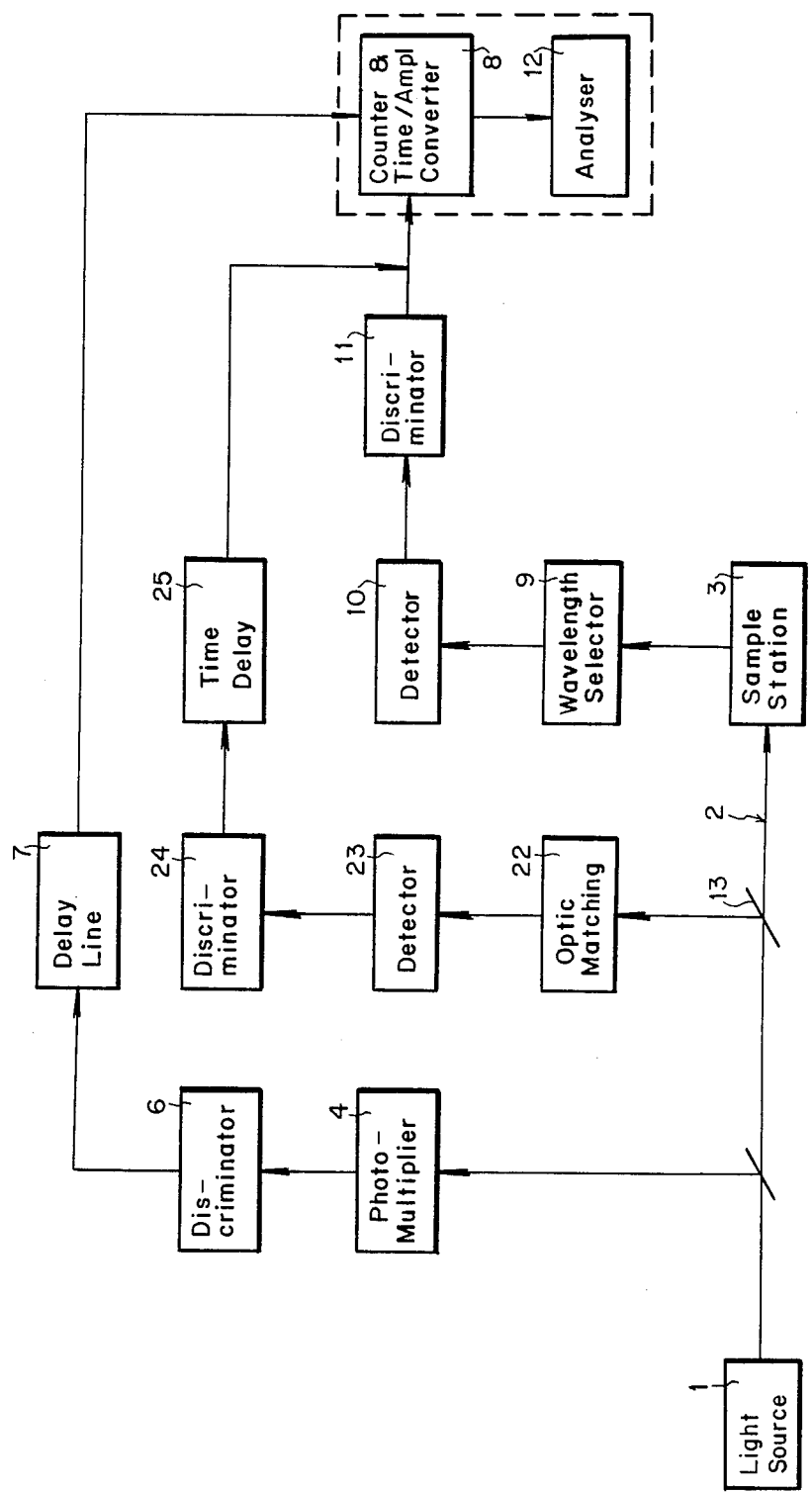
FIG. 3 illustrates a second embodiment of apparatus according to the present invention.

In the FIG. 3 embodiment the excitation pulse profile determining means incorporates its own detector 23 associated with input optics 22 whereby the geometry of photocathode illumination can be matched with that of detector 10. The output of detector 23 is passed to a time-delay means 25 (in this instance operating electronically) via a threshold discriminator 24 functioning correspondingly to discriminator 11 and the output of means 25 is delivered to the input of means 8,12 in an OR configuration. The FIG. 3 embodiment has the advantage over the FIG. 2 embodiment that the separation of the detection function to two separate detectors 10,23 enables the impulse response of these detectors to be closely matched despite the fact that the detectors are subjected to events in different spectral wavelength regions.

Figure 4:
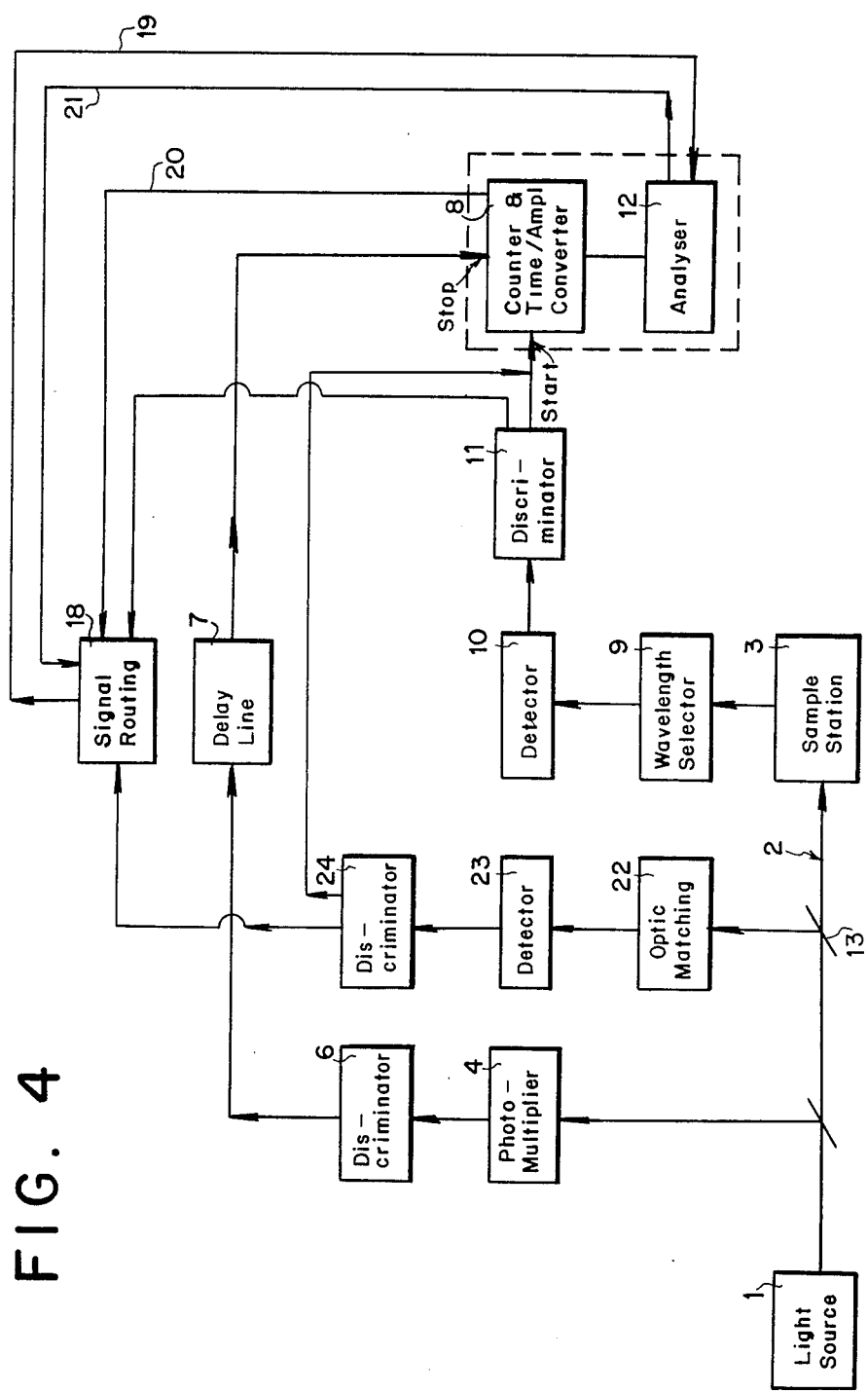
FIG. 4 illustrates a third embodiment of apparatus according to the present invention.

The FIG. 4 embodiment is similar to the FIG. 3 embodiment except for the absence of the time-delay means 25 and the introduction of signal-routing circuitry 18 receiving input signals from discriminators 11,24 and in consequence controlling analyser 12 via line 19 to receive and store excitation pulse profile events separately from fluorescence photon events thereby enabling discrimination between these two measures. Line 21 provides a reset signal to circuitry 18 following storage of each event. Line 20 provides a confirmatory start signal.

Figure 5:
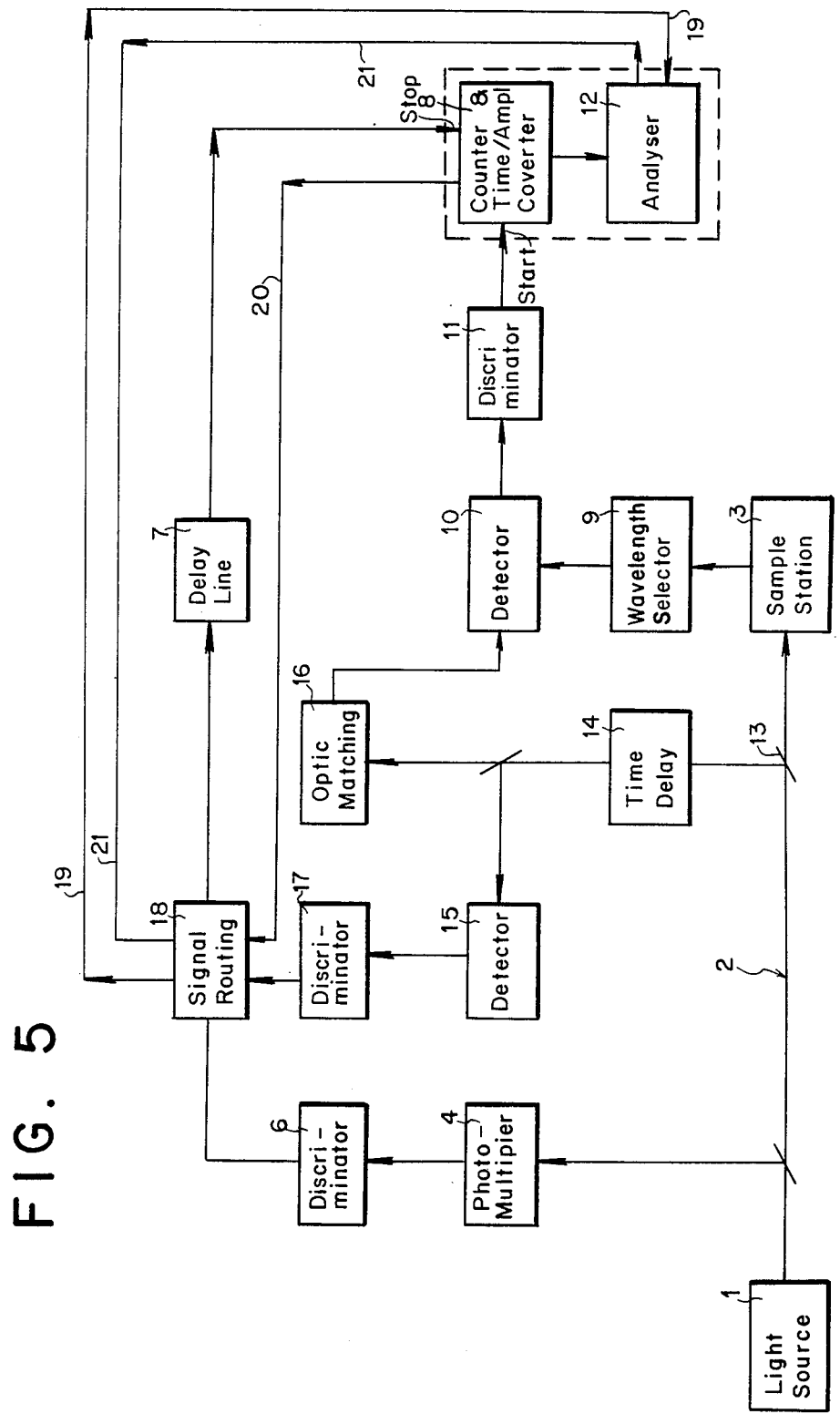
FIG. 5 illustrates a fourth embodiment of apparatus according to the present invention.

The FIG. 5 embodiment is similar to the FIG. 2 embodiment in that only a single detector 10 is utilised and as regards signal-routing circuitry 18 is similar to the FIG. 4 embodiment but in this instance the input signals to circuitry 18 are derived from device 8 on the one hand and discriminator 17 at the output of detector 15 coupled to the output of delay means 14 on the other hand.

It will be understood that circuitry 18, for example, incorporates a latch which is set to logic 1 or logic 0 depending upon whether a fluorescence event or an excitation event is signalled. The condition of this latch determines the nature of the signal on line 19. The latch is reset by the signal on line 21.

As regards the FIG. 4 embodiment which does not incorporate the time-delay means 25 separation of the two kinds of events is undertaken on the statistical basis that because events are relatively rare the simultaneous presence of both fluorescence and excitation events is exceptional. On this basis either one event only may be recorded as a fluorescence event or both events may be rejected (and neither recorded).

It will now be appreciated that in its simplest form the present invention provides quasi simultaneous measurement (i.e. on a time-shared basis) of both fluorescence characteristics and excitation pulse profile thereby enabling automatic correction of the data collected for fluorescence characteristics to account for variations in the excitation source; both long term and short term variations. This has the additional advantage that such measurement of excitation pulse profile is undertaken independently of the sample station so that special environments thereat can be maintained as required. In a more complicated form the invention enables matching of the photodetectors to provide similar impulse transfer functions to the received events thereby rendering the detector outputs independent of the spectral wavelength differences between the fluorescence events and the excitation pulse profile events.

We claim:

1. Apparatus for measuring fluorescence characteristics of a material sample, comprising:
a sample station for receiving a material sample the fluorescence characteristics of which are to be measured,
fluorescence photon-event receiving means coupled to said sample station to receive single photon events arising therefrom, an excitation light source capable of emitting a train of excitation light pulses towards said sample station so as to irradiate a sample therein, excitation pulse profile determining means, sensitive to said train of excitation light pulses and having sufficient attenuation to provide an output event count rate compatible with the fluorescence photon event count rate, detecting means coupled to receive the output of said receiving means and the output of said determining means, synchronization means operable by said excitation light source to generate a train of synchronization pulses, measuring means coupled to the output of said detecting means and to the output of said synchronization means and operable according to the photon correlation technique to provide on a time-shared basis a measure of said fluorescence characteristics and a measure of said excitation pulse profile, said measuring means including discrimination means enabling said excitation pulse profile measure to be distinguished from said fluorescence characteristics measure.

2. Apparatus as claimed in claim 1, characterised in that the detecting means comprises a single detector receiving both sets of input events.

3. Apparatus as claimed in claim 1, characterised in that the detecting means comprises a pair of detectors each receiving only one set of input events.

4. Apparatus as claimed in any preceding claim, characterized in that a time-delay means is provided in one of said receiving means and said determining means, said time-delay means being adapted to introduce a time-delay of less than one half the pulse repetition period of the excitation light source but substantially greater than the fluorescence decay time of the sample.

5. Apparatus as claimed in claim 1, characterized in that the measuring means is arranged to measure the time interval at which an event occurs in relation to a synchronization pulse.

6. Apparatus as claimed in claim 5, characterized in that the measuring means converts said measure of time interval proportionately to amplitude measures.

7. Apparatus as claimed in claim 5, characterized in that the measuring means measures the accumulated number of events occurring at each time interval over the duration of the measurement process.

8. Apparatus as claimed in claim 1, characterized in that the discrimination means is provided by electronic routing circuitry whereby fluorescence events are directed into different storage channels from excitation pulse profile events.

9. Apparatus as claimed in claim 1, characterized in that the discrimination means is provided by a single storage channel in which excitation pulse profile events are stored at longer time interval indicia than fluorescence events.

* * * * *